United States Patent [19]
Rosati et al.

[11] Patent Number: 5,100,018
[45] Date of Patent: Mar. 31, 1992

[54] PROBE COVER DISPENSER

[75] Inventors: Robert J. Rosati; Fred W. Bacher, both of San Diego, Calif.

[73] Assignee: IVAC Corporation, San Diego, Calif.

[21] Appl. No.: 595,813

[22] Filed: Oct. 11, 1990

[51] Int. Cl.⁵ ............................................. B65H 3/00
[52] U.S. Cl. .................................... 221/6; 221/191; 221/226; 221/228; 221/232; 221/239; 221/266; 221/270; 221/155
[58] Field of Search ............... 221/2, 6, 191, 194–196, 221/197–198, 208, 224, 226, 228, 232, 236, 239, 263, 255–256, 266, 268, 270–271, 279, 155, 287; 128/664

[56] References Cited

U.S. PATENT DOCUMENTS

| | | | |
|---|---|---|---|
| 557,553 | 4/1896 | Chillberg | 221/155 |
| 1,678,355 | 7/1928 | Roberts | 221/271 |
| 2,577,344 | 12/1951 | Masure | 221/155 |
| 3,162,322 | 12/1964 | Gilbertson | 221/271 |
| 3,191,588 | 6/1965 | Thew | 221/271 |
| 3,422,989 | 1/1969 | Long | 221/198 |
| 3,471,056 | 10/1969 | Kovac | 221/155 |
| 4,101,053 | 7/1978 | Mast | 221/232 |
| 4,602,642 | 7/1986 | O'Hara et al. | 128/664 |
| 4,784,149 | 11/1988 | Berman et al. | 128/664 |
| 4,790,324 | 12/1988 | O'Hara et al. | 128/664 |
| 4,911,559 | 3/1990 | Meyst et al. | 374/158 |
| 4,932,789 | 6/1990 | Egawa et al. | 374/126 |

FOREIGN PATENT DOCUMENTS 485376 10/1953 Italy ............................. 221/271

Primary Examiner—David H. Bollinger
Attorney, Agent, or Firm—Fulwider, Patton, Lee and Utecht

[57] ABSTRACT

A storage chamber large enough to store a predetermined number of probe covers is formed into a dispenser body. A spring biases the probe covers toward one end of the chamber at which is located a slide. The slide has an indentation used to retrieve a single probe cover from the chamber at a time when aligned with the chamber. Located in the indentation is an aperture tube for receiving a probe of the instrument to be covered. The probe is pressed into the probe cover and into the aperture thus causing the probe cover to stretch and cover the probe. A flange formed on the slide is pressed by a user to align the indentation of the slide with the chamber. The slide is spring loaded so that releasing the flange will result in the slide moving such that the indentation is located outside the chamber and the retrieved probe cover can be applied to the instrument. A door in the dispenser is raised to allow access to the chamber for the insertion of a stack of probe covers. Probe covers in each stack are held together with a removable band. After inserting a stack of probe covers in the chamber, the door is closed and a pull tab on the band pulled to remove the entire band from the stack. A quantity indicator is provided which allows the user to see the quantity of probe covers remaining in the chamber without opening the door.

18 Claims, 4 Drawing Sheets

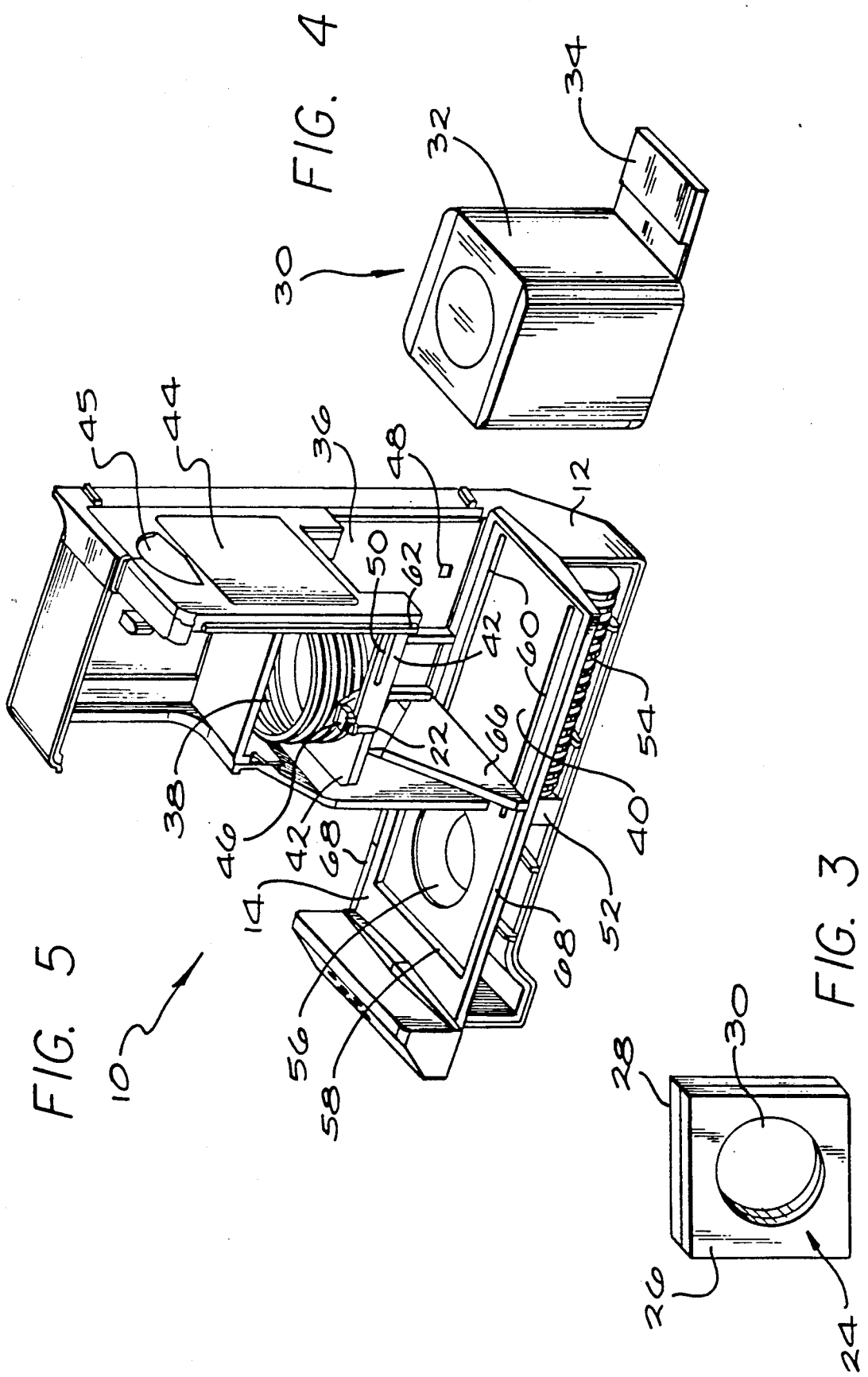

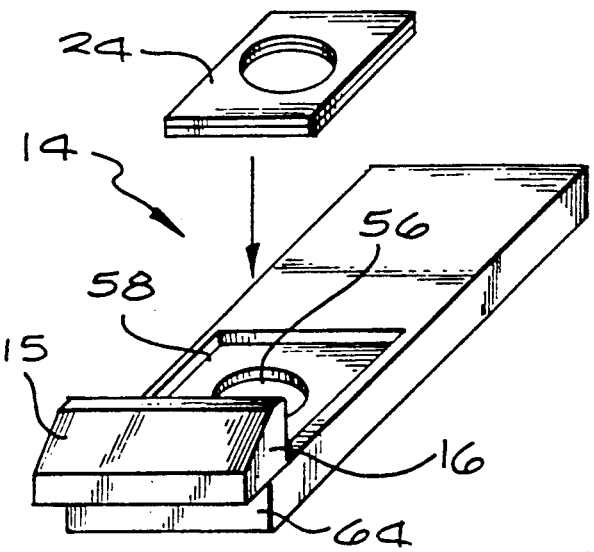
FIG. 6A
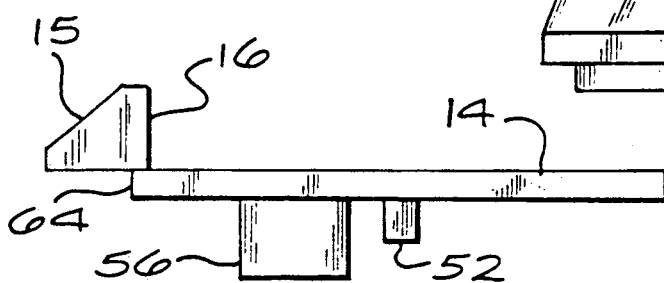
FIG. 6B
FIG. 7
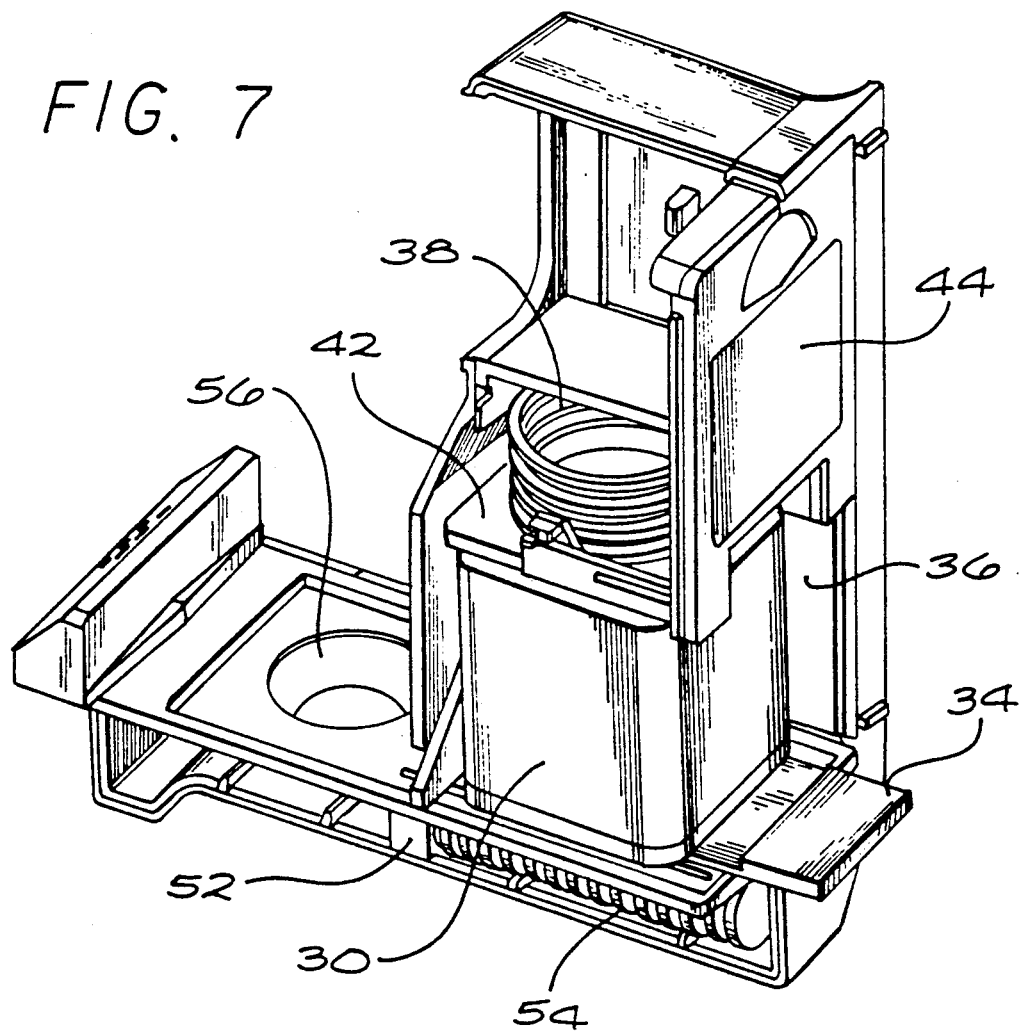

PROBE COVER DISPENSER

BACKGROUND

The invention is related generally to dispensers and more particularly, to dispensers for the controlled handling of medical items.

Medical instruments of the type which make contact with a portion of the body of a patient when taking a measurement typically include a probe. Thermometers, and especially infrared thermometers, are examples of such contact instruments and their probes are inserted into body cavities, such as the mouth or the ear. The use of such contact type instruments among multiple patients may result in the spreading of infections and diseases unless precautions are taken. One precaution that has been employed is the use of a speculum or a disposable cover placed over the probe just prior to the instrument's use on a patient. After the required measurement has been taken, the speculum or probe cover is discarded. This technique has been found to be very effective and disposable speculums are widely used.

One type of disposable probe cover comprises a sandwich of cardboard and a stretchable film. The cardboard has a central aperture, over which the film extends, for receiving the probe. As the probe is pressed through the aperture, the film stretches to cover the probe. The cardboard supports the film as it is stretched over the probe tip.

The use of such a probe cover must be accompanied by appropriate handling techniques so that the cover itself does not become contaminated before use. For example, storage of the probe covers should involve precautions which protect the stretchable film from being exposed to contamination. Selection and application of a probe cover to a probe should be performed in a way that does not require or expose the stretchable film to touching the body of the user of the instrument.

Those concerned with the use of disposable probe covers have recognized the need for techniques which secure unused probe covers from contamination prior to use and which provide means to handle and to apply the probe cover to the probe of the instrument without contaminating the probe cover. The present invention fulfills those needs.

SUMMARY OF THE INVENTION

Briefly and in general terms, the present invention provides a new and improved dispenser embodying novel methods and apparatus for securing unused probe covers from contamination and for dispensing such probe covers at the appropriate time. By the arrangement in accordance with the invention, the probe covers may be retrieved from storage and applied to the probe of a contact-type instrument without the need for the user to handle the probe cover itself.

Basically, the present invention is directed to a dispenser having a storage chamber large enough to store multiple probe covers. A spring disposed in that dispenser biases the probe covers toward the opposite end of the chamber at which is located a probe cover slide. The slide is used to transport a probe cover from the chamber to a position where it may be applied to the probe of an instrument. The slide in one embodiment is relatively flat and includes an indentation adjacent an engagement flange. The indentation is approximately the size of a probe cover and has a depth approximately equal to that of a single probe cover. The engagement flange is shaped to receive a digit of a user for applying force to the flange to cause the probe cover slide to move between two positions. The first position is an engaged position where the indentation of the slide is aligned with the chamber to receive a probe cover for retrieval and the second position is the application position where the probe cover is made available for application to the probe.

When the slide is in the first position, the chamber spring forces a single probe cover into the indentation of the slide. The indentation captures the probe cover and fixes it in position in relation to the slide. The slide is then moved to the second position. Because the indentation is approximately the same size as the probe cover, the captured probe cover will move with the slide but a wiper mounted in the body of the dispenser and riding on rails formed on the slide blocks other probe covers in the chamber from leaving. In one embodiment, the slide is biased toward the second position with a spring.

The indentation of the slide further includes an aperture tube which approximates the size of the probe of the instrument to which the probe cover is to be applied. When the slide is located in the second position, the probe may be inserted in contact with the cover and pressed into the aperture tube thus stretching the cover over the probe. The aperture tube has soft and lubricious surfaces to aid in applying the probe cover to the probe and reduce the possibility of probe cover damage during application.

A band is used to hold the probe covers in a stack. The band has a pull tab which is pulled by the user when the stack is in place in the chamber with the door closed. The pull tab protrudes from a relieved area in the lower portion of the door. The operator pulls the tab thus removing the band and freeing the probe covers for retrieval by the slide.

The door includes an arm to engage the chamber spring such that the spring is compressed when the door is moved to the open position. In this configuration, a new stack of probe covers can be placed in the chamber.

In one embodiment, the dispenser includes an instrument receptacle which may be used to store the instrument with the dispenser. A stabilizing flange is added to assist the dispenser in remaining upright on a resting surface.

These and other objects and advantages of the invention will become apparent from the following more detailed description, when taken in conjunction with the accompanying drawings of illustrative embodiments.

BRIEF DESCRIPTION OF THE DRAWINGS

FIG. 3 is a view of a probe cover usable in the dispenser of FIGS. 1 and 2;

FIG. 4 is a perspective view of a stack of probe covers held together with a band which has a pull tab;

FIG. 5 is a cutaway perspective view of a dispenser in accordance with the principles of the invention showing the chamber and chamber spring, the door and the slide and slide spring;

FIGS. 6A and 6B are views of a slide usable in the embodiment of FIG. 5;

FIG. 7 is a view of a dispenser having a stack of probe covers loaded into the chamber but with the loading door in the open position;

DESCRIPTION OF THE PREFERRED EMBODIMENTS

Figure 1:
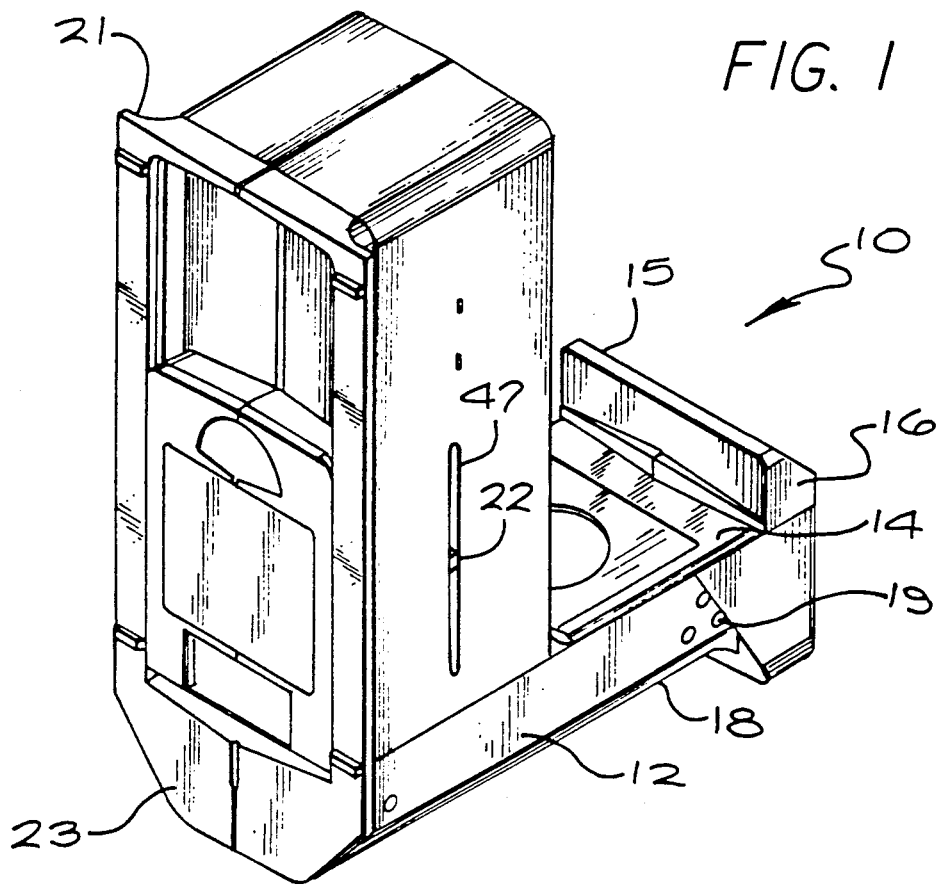
FIG. 1 is a perspective view of a probe cover dispenser incorporating the principles of the invention.

In the following description, like reference numerals will be used to refer to like or corresponding elements in the different figures of the drawings. Referring now to the drawings, and particularly to FIG. 1, there is shown a probe cover dispenser 10 with a body section 12 and a movable probe cover slide 14. The slide 14 includes an engagement flange 16 for receiving a user's digit, such as the thumb, to cause the slide to move as will be discussed in more detail below. The body 12 has a rounded handling section 18 with which a user may comfortably grip the dispenser 10. Raised bumps 19 may be included on the handling section 18 to aid in gripping.

Figure 2:
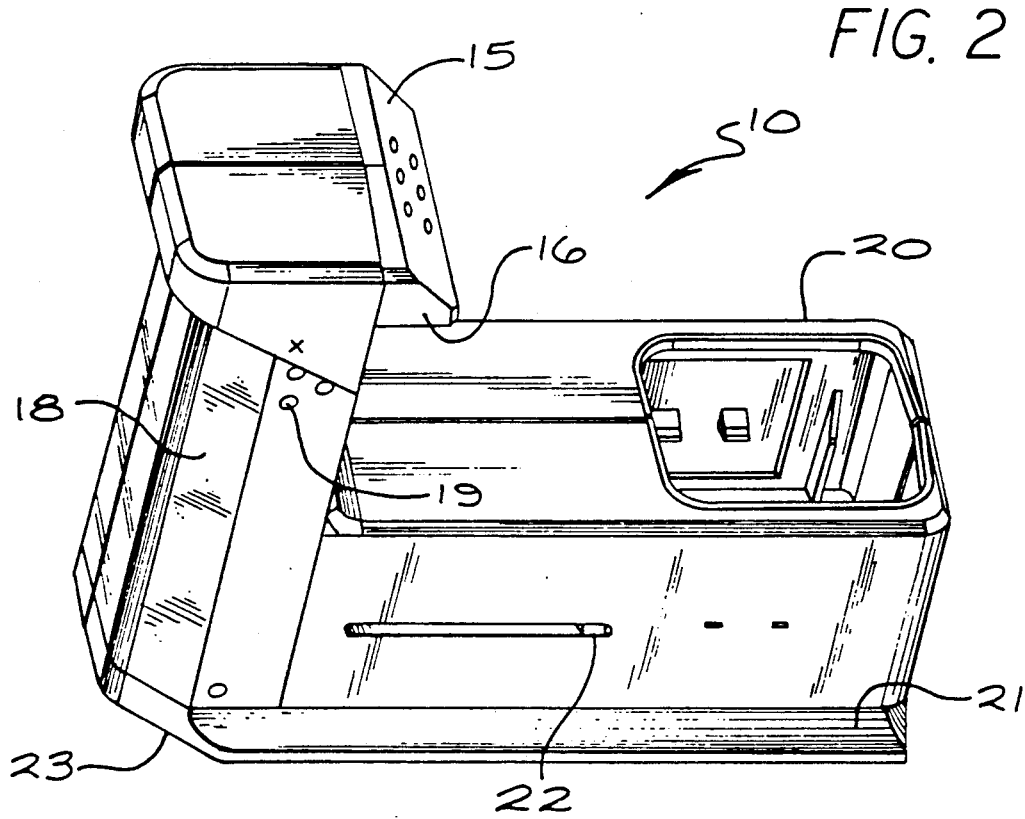
FIG. 2 is a perspective view of a probe cover dispenser incorporating the principles of the invention with an integral instrument receptacle.

Referring now to both FIGS. 1 and 2, included with the dispenser 10 is an instrument receptacle 20. This receptacle 20 may be used to contain an instrument for which the probe covers would be dispensed by the dispenser 10. A stabilizing flange 21 assists in maintaining the dispenser 10 upright when it is placed on a resting surface. The flange extends outward from the bottom surface 23 of the dispenser 10 thus giving more surface area to result in increased stability. Also shown in FIGS. 1 and 2 is a quantity indicator 22 for indicating the number of probe covers remaining in the dispenser. The quantity indicator will also be discussed in further detail below.

The slide 14 has a flange 16 formed on it to accept a digit, such as a thumb, of a user. The flange has a slanted portion 15 for receiving the digit. It has been found that a slant functions well to impart sufficient force considering the angle at which the thumb would be positioned when a user's hand is wrapped around the handling section 18 of the dispenser 10. However, other shapes of the digit contact point 15 of the flange 16 are possible and may function equally well. The placement of the flange 16 is selected in respect to the distance around the body of the dispenser 10 so that an average user's thumb would conveniently engage the flange 16. Raised bumps 17 or some other grip enhancing means may be added to the surface 15.

Referring now to FIG. 3, there is shown a probe cover 24 comprising two layers. In this embodiment, the support layer 26 is formed of paper and the second layer 28 is formed of a plastic film such as low density polyethylene. The depth of each layer is exaggerated in this figure for the purpose of clarity. A central aperture 30 is formed in the layers to accept the probe of the instrument.

Referring now to FIG. 4, a stack 30 of approximately fifty probe covers is shown. Holding the stack together is a band 32 of material such as cellophane. The band 32 has at one of its ends a pull tab 34 for use as will be described below. The other end of the band 32 is welded or otherwise attached to the band itself so as to hold the stack of probe covers together. This stack 30 will be inserted into the dispenser 10 as is described below. The band 32 in this embodiment is wide enough to completely cover the apertures of the probe covers, thus protecting that portion of the stretchable film which will be in contact with a patient from contamination. By means of this arrangement, the banded stack 30 may be handled by a user without contaminating the film which forms the actual probe cover.

Referring now to FIG. 5, a cutaway, perspective view of the dispenser 10 is presented. The dispenser has a probe cover chamber 36 within which the stack 30 of probe covers is stored. At the top of the chamber 36 is a chamber spring 38. The spring 38 is used to bias the stack of probe covers towards a slide 40 located at the bottom of the chamber 36. The spring 38 is coupled to a pressure plate 42 which rests against the top probe cover in the stack. The pressure plate 42 is shown in a retracted position in FIG. 5 due to the arm 42 which is part of the chamber door 44 having engaged the retraction protrusion 46 which is rigidly mounted on the pressure plate 42. The quantity indicator 22 is mounted on this protrusion 46.

As can be more clearly seen by referring to FIG. 1, the quantity indicator 22 is visible through a slot 47 formed in the body 12 of the dispenser. In the embodiment shown, two quantity indicators are included, one on each side of the dispenser.

When sliding the door 44 to the raised position shown in FIG. 5, the arm 42 contacts the retraction protrusion 46 which then accompanies the door 44 into a raised position. In the embodiment of FIG. 5, a second arm is located on the other side of the door and likewise engages a second retraction protrusion mounted to the pressure plate 42. An indentation 45 is formed into the door 44 to facilitate movement of the door upwards.

Also shown in FIG. 5 is a locking tab 48 formed in the chamber 30 for engaging a bump 50 in the door arm 42 when the door is in the lowered position. Upon the locking tab engaging the bump, the door will be held in the closed or lowered position. The sides of the tab 48 are angled such that a predetermined upward force on the door will cause the bump to move from engagement with the tab 48 and the door can then be more easily raised. Although only one tab 48 is shown in FIG. 5 and that tab is shown as being located on the opposite side of the chamber 36 from the arm 42 shown, this view is for the purpose of clarity only. In one embodiment, there exist two arms, each with a bump and two tabs on opposing walls of the chamber for engaging respective bumps of the two arms.

Also shown in FIG. 5 is the slide 14 in its relaxed position. Mounted to or formed as part of the slide is a spring block 52 for engaging a slide spring 54 mounted to the body 12 of the dispenser. The spring 54 biases the slide 14 into the relaxed position where the aperture tube 56 of the slide 14 lies outside the chamber 30. The aperture tube 56 is formed into the slide 14 and its opening and depth are of sizes to accept the probe of the instrument which the dispenser services.

Referring to FIGS. 6A and 6B, the slide 14 includes an indentation 58 which is approximately the same size as the probe cover 24 including the depth dimension. This indentation 58 is used to accept only a single probe cover from the stack of probe covers stored in the chamber 36. Located in the indentation 58 is the aperture tube 56 used for receiving a probe during the process of applying the probe cover. The aperture tube 56 has relatively soft and very lubricious surfaces which prevent the stretched film of the probe cover from experiencing high, localized stresses. These stresses can tear the film during probe insertion or withdrawal from the slide aperture tube 56. One substance found to function well on the surfaces of the aperture tube 56 is a Teflon coating. The depth of the handling section 18 of the dispenser (FIG. 1) and the size of the aperture tube 56 are selected so that the probe may be inserted far enough to stretch the probe cover entirely over the probe. Thus, no user contact of the probe cover is necessary.

Referring again to FIG. 5, the slide 14 also includes two grooves 60 extending from the indentation 58 to the rear of the slide. These grooves engage protrusions 62 on the bottom of the door and prevent probe covers in the chamber stack from exiting under the door during movement of the slide 14. Under the flange 16 of the slide 14 is a stop lip 64 which stops the movement of the slide 14 caused by the spring 54 by engaging a portion 65 (see FIG. 8) of the body of the dispenser.

Referring now to FIG. 7, a dispenser 10 is shown with a stack 30 of probe covers in place in the chamber 36. The door 44 is still holding the pressure plate 42 in a raised position. The pull tab 34 of the band 32 is shown protruding from the chamber 36.

Figure 8:
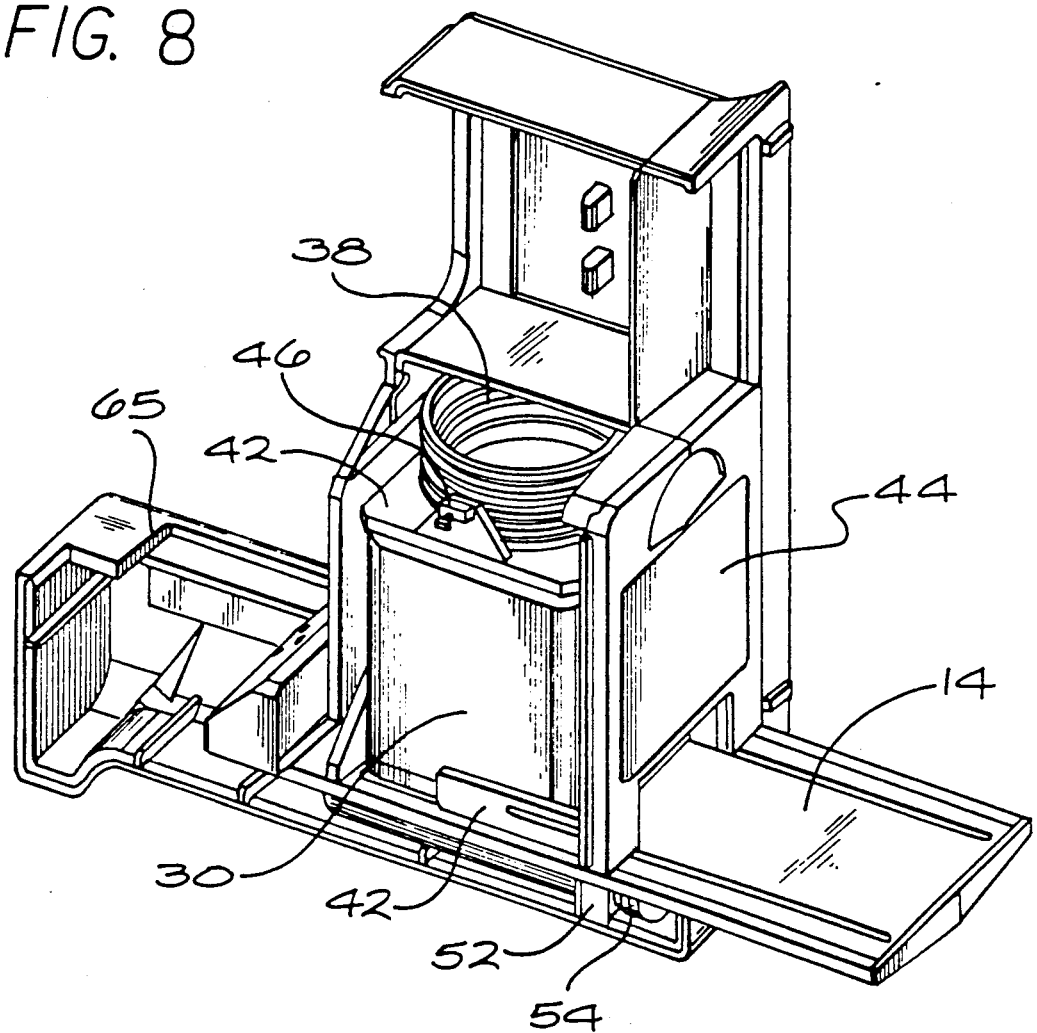
FIG. 8 is a view of the dispenser of FIG. 7 with the door in the closed position and the slide moved so that the indentation is aligned with the chamber.

Referring now to FIG. 8, a dispenser in accordance with the principles of the invention is shown with the door 44 in the closed position. The pull tab shown in FIG. 7 has been pulled with sufficient force to pull the entire band from the stack 30 of probe covers, thus freeing them for retrieval by the slide 14. The arm 42 has disengaged the pressure plate protrusion 46 and the spring 38 has forced the pressure plate 42 into contact with the probe cover stack 30. The slide 14 has been moved so that the indentation is aligned with the stack of probe covers. The slide spring 54 has been compressed by the spring block 52. Although not visible from FIG. 8, the pressure plate has forced one of the probe covers into the indentation of the slide for withdrawal from the chamber.

A further feature is shown by referral to FIG. 5. A function of the embodiment of FIG. 5 is to retrieve only a single probe cover at a time. The indentation of the slide 14 is used to capture that single probe cover and a wiper 66 is used to retain the remaining probe covers in the chamber 36 while that single probe cover is retrieved. The flat bottom of the wiper 66 rests on rails 68 which are located on either side of the slide 14. The rails are high enough to allow the probe cover captured by the indentation of the slide 14 to pass under the wiper but low enough so that only that probe cover can leave the chamber when the slide is moved.

Figure 9:
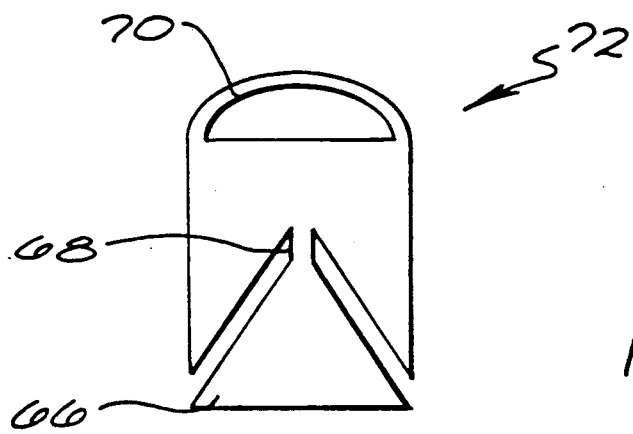
FIG. 9 is a view of a wiper for retaining the probe covers in the chamber except for the cover being retrieved.

Referring now to FIG. 9, a wiper 66, mounting hinge 68 and spring 70 are shown. The wiper 66 is triangular in shape and is mounted at the top of its triangular shape with a hinge 68 which permits a tilting action of the wiper to compensate for manufacturing tolerances. To force the wiper 66 into contact with the rails 68 on the slide 14, the spring 70 is positioned so that downward pressure is applied. Thus the spring 70 will be compressed somewhat and that compression will force the flat surface of the wiper 66 into contact with the rails. By correct choice of the size of the spring 70, compensation for manufacturing tolerances is possible. The spring 70, hinge 68 and wiper 66 may be formed as a single piece and be referred to as a wiper assembly 72.

Thus there has been provided a new and useful dispenser for use in handling medical devices such as probe covers without manually touching those devices. The combination of the invention greatly reduces the possibility of contamination of the probe covers which is possible with prior manual handling techniques.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A probe cover dispenser comprising:
   a chamber for holding a predetermined quantity of probe covers each having selected size dimensions;
   a receiving slide movably mounted in relation to a first end of the chamber and having an indentation of a size approximately corresponding to the size dimensions of one of the probe covers to receive a single probe cover from the chamber, the slide having a first position at which the indentation is aligned with the probe covers disposed in the chamber and a second position at which the indentation is disposed at a position outside the chamber;
   a first spring adapted to urge the probe covers which are disposed in the chamber into contact with the slide;
   a second spring coupled to the slide to urge it to the second position; and
   a flange disposed on the slide and adapted to receive an operator's digit which may be applied to move the slide into the first position.

2. The dispenser of claim 1 further comprising a pressure plate disposed in the chamber in contact with the first spring and which applies uniform pressure upon the probe covers in response to urging from the first spring to thereby urge the probe covers into contact with the slide.

3. The dispenser of claim 2 further comprising a quantity indicator adapted to indicate the number of probe covers remaining in the chamber.

4. The dispenser of claim 3 wherein the quantity indicator comprises:
   a protrusion formed on the pressure plate which moves with the pressure plate; and
   a slot formed in the body of the dispenser through which the protrusion may be seen.

5. The dispenser of claim 3 wherein the quantity indicator comprises a first reference mark fixed in position in relation to the chamber and a second reference mark coupled to the pressure plate, the first reference mark being positioned so that when no probe covers remain in the chamber, the first and second marks will be aligned.

6. The dispenser of claim 1 wherein:
   the second position of the slide is disposed outside of the chamber at a position where the probe may be received by the probe cover residing in the indentation; and
   further comprising an aperture formed in the indentation, the size of the aperture is proportional to the size of the probe for receiving the probe after it makes contact with the probe cover so that the probe cover is stretched over the probe.

7. The dispenser of claim 6 wherein the aperture comprises an aperture tube disposed below the aperture when in the second position for receiving the probe, the aperture tube having a lubricious surface.

8. The dispenser of claim 1 wherein the slide comprises a stop lip which stops the slide from being urged beyond the second position by the first spring.

9. The dispenser of claim 1 wherein the chamber includes a loading door having an open position in which the probe covers may be loaded into the chamber, and a closed position closing the chamber, and wherein the door is coupled to the first spring and is urged into the closed position by the first spring so that when the door is opened, the first spring is compressed so that probe covers may be loaded into the chamber.

10. The dispenser of claim 1 wherein the slide is mounted in a support having a rounded shape to accept the hand of an operator and the flange is shaped to accept the thumb of the operator for forcing the slide to move to the first position.

11. The dispenser of claim 1 further comprising a base connected to the slide, the base having an instrument receptacle formed therein for accepting the handle of an instrument.

12. The dispenser of claim 1 further comprising a body in which the chamber is disposed, the body including a bottom surface and a stabilizing flange formed on the outside of the bottom surface of the body and stabilizing the dispenser when the bottom surface is placed upon a bearing surface.

13. A probe cover dispenser for applying probe covers to the probe of an instrument, comprising:
  a chamber for holding a predetermined quantity of probe covers each having selected size dimensions;
  a receiving slide movably mounted in relation to a first end of the chamber and having an indentation of a depth and size approximately corresponding to the size dimensions of one of the probe covers to receive a single probe cover from the chamber, the slide having a first position at which the indentation is aligned with the probe covers disposed in the chamber and a second position at which the indentation is disposed at a position outside the chamber;
  an aperture formed in the indentation, the size of the aperture is proportional to the size of the probe for receiving the probe after it makes contact with the probe cover so that the probe cover is stretched over the probe;
  a first spring adapted to urge the probe covers which are disposed in the chamber into contact with the slide;
  a second spring coupled to the slide to urge it to the second position; and
  a flange disposed on the slide and adapted to receive an operator's digit which may be applied to move the slide into the first position.

14. The dispenser of claim 13 wherein the aperture comprises an aperture tube disposed below the aperture when in the second position for receiving the probe, the aperture tube having a lubricious surface.

15. A probe cover dispenser comprising:
  a body having a chamber for holding a predetermined quantity of probe covers each having selected depth and size dimensions;
  a receiving slide movably mounted in relation to a first end of the chamber and having an indentation of a depth and size approximately corresponding to the depth and size dimensions of one of the probe covers to receive a single probe cover from the chamber, the slide having a first position at which the indentation is aligned with the probe covers disposed in the chamber and a second position at which the indentation is disposed at a position outside the chamber;
  a first spring adapted to urge the probe covers which are disposed in the chamber into contact with the slide;
  a pressure plate disposed in the chamber in contact with the first spring and which applies uniform pressure upon the probe covers in response to urging from the first spring to thereby urge the probe covers into contact with the slide;
  a second spring coupled to the slide to urge it to the second position;
  a flange disposed on the slide and adapted to receive an operator's digit which may be applied to move the slide into the first position; and
  a quantity indicator adapted to indicate the number of probe covers remaining in the chamber, the quantity indicator including a protrusion formed on the pressure plate which moves with the pressure plate and a slot formed in the body of the dispenser through which the protrusion may be seen.

16. A probe cover dispenser comprising:
  a chamber for holding a predetermined quantity of probe covers each having selected depth and size dimensions; a receiving slide movably mounted in relation to a first end of the chamber and having an indentation of a depth and size approximately corresponding to the depth and size dimensions of one of the probe covers to receive a single probe cover from the chamber, the slide having a first position at which the indentation is aligned with the probe covers disposed in the chamber and a second position at which the indentation is disposed at a position outside the chamber where the probe may be received by the probe cover residing in the indentation, an aperture being formed in the indentation, the size of the aperture being proportional to the size of the probe for receiving the probe after it makes contact with the probe cover so that the probe cover is stretched over the probe;
  a first spring adapted to urge the probe covers which are disposed in the chamber into contact with the slide;
  a second spring coupled to the slide to urge it to the second position; and
  a flange disposed on the slide and adapted to receive an operator's digit which may be applied to move the slide into the first position.

17. The dispenser of claim 16 wherein the aperture comprises an aperture tube disposed below the aperture when in the second position for receiving the probe, the aperture tube having a lubricious surface.

18. A probe cover dispenser comprising:
  a chamber for holding a predetermined quantity of probe covers each having selected depth and size dimensions, the chamber including a loading door having an open position in which the probe covers may be loaded into the chamber, and a closed position closing the chamber;
  a receiving slide movably mounted in relation to a first end of the chamber and having an indentation of a depth and size approximately corresponding to the depth and size dimensions of one of the probe covers to receive a single probe cover from the chamber, the slide having a first position at which the indentation is aligned with the probe covers disposed in the chamber and a second position at which the indentation is disposed at a position outside the chamber;

a first spring adapted to urge the probe covers which are disposed in the chamber into contact with the slide, the door being coupled to the first spring and being urged into the closed position by the first spring so that when the door is opened, the first spring is compressed so the probe covers may be loaded into the chamber;

a second spring coupled to the slide to urge it to the second position; and a flange disposed on the slide and adapted to receive an operator's digit which may be applied to move the slide into the first position.

* * * * *